United States Patent [19]

Lovrecich

[11] Patent Number: 5,008,114
[45] Date of Patent: Apr. 16, 1991

[54] PHARMACEUTICAL COMPOSITIONS WITH CONTROLLED RELEASE, AND A METHOD FOR THEIR PREPARATION

[75] Inventor: Mara L. Lovrecich, Trieste, Italy

[73] Assignee: Vectorpharma International S.p.A., Trieste, Italy

[21] Appl. No.: 276,489

[22] Filed: Nov. 28, 1988

[30] Foreign Application Priority Data

Apr. 8, 1988 [IT] Italy ............................... 20145 A/88

[51] Int. Cl.$^5$ .......................... A61K 9/14; A61K 9/26
[52] U.S. Cl. .................................... 424/484; 424/423;
424/425; 424/443; 424/464; 424/465; 424/489;
424/469; 424/468; 424/452
[58] Field of Search ............... 424/423, 468, 469, 443,
424/464, 465, 484, 425

[56] References Cited

U.S. PATENT DOCUMENTS

| 3,923,969 | 12/1975 | Baukel et al. | 424/468 |
|---|---|---|---|
| 4,254,099 | 3/1981 | Asmussen et al. | 424/469 |
| 4,775,535 | 10/1988 | Lowey | 424/469 |
| 4,781,858 | 11/1988 | Mizukami et al. | 424/469 |
| 4,834,978 | 5/1989 | Nuwayser | 424/423 |

Primary Examiner—Thurman K. Page
Assistant Examiner—James M. Spear
Attorney, Agent, or Firm—Parkhurst, Wendel & Rossi

[57] ABSTRACT

Pharmaceutical compositions including a microporous support and an active substance incorporated therein, the incorporation of the active substance being effected by adding the microporous support to a solution of the active substance, stirring the mixture obtained for at least 70 hours at ambient temperature and finally evaporating the solvent slowly.

13 Claims, No Drawings

PHARMACEUTICAL COMPOSITIONS WITH CONTROLLED RELEASE, AND A METHOD FOR THEIR PREPARATION

FIELD OF THE INVENTION

This invention relates to pharmaceutical compositions with controlled release in which the active substance is incorporated in a microporous support.

PRIOR ART

It is known to use microporous supports for incorporating active substances of pharmaceutical type to improve their useful properties.

For example, in order to increase the release rate of poorly soluble medicaments it has been proposed to incorporate them in a porous material either operating with a solution of said medicaments (European Patent Application No. 0163178) or operating by dry grinding (European Patent Application No. 0129893).

Again, various authors [DE Nos. 3230736, 2163034, U.S. Pat. No. 3,923,969, Rupprecht H et al., Colloid Polym. Sci. (1977) 255-3, pp. 276-84] have suggested the use of porous silicas to obtain prolonged release of the medicament by utilizing the dimensions and shape of the pores or the properties of the medicament adsorption on the silica surface.

In all the stated methods, the medicament is present either in the amorphous state or as microcrystals (dimensional range of the order of micrometers).

SUMMARY OF THE INVENTION

In the present invention the medicament is structured in crystalline form with crystals having a size of the order of nanometers.

This dispersion of the product in nanocrystals enables the chemical and physical stability of the medicament to be maintained and results in a sharp improvement in the biopharmaceutical properties of the system.

The present invention relates to pharmaceutical compositions and to the method for their preparation.

The pharmaceutical compositions comprise a microporous support and an active substance incorporated therein and are characterized in that the active substance is distributed in the support pores as nanocrystals, the microporous support has pores of an average diameter between 5 and 150 nm, a specific surface area of between 30 and 600 m²/g, a particle diameter of less than 200 microns and the content of the active substance is between 4 and 60% by weight.

The method is characterized by adding a microporous support to a solution of the active substance, stirring at ambient temperature for at least 70 hours and slowly evaporating the solvent under reduced pressure.

DETAILED DESCRIPTION OF THE INVENTION

The pharmaceutical compositions according to the invention are prepared by the following method and have the characteristics stated hereinafter.

A solution of the active substance is prepared, a microporous support is added to this solution and the mixture obtained is kept stirring at ambient temperature for a prolonged time, at least 70 hours and preferably between 90 and 100 hours. After this treatment the solvent is evaporated slowly.

If the stirring time is less than 70 hours the desired active substance release characteristics are not obtained, whereas if the time is extended beyond 100 hours the improvement is negligible.

Preferred active substances for the compositions according to the invention are those of low water-solubility, which are released from the compositions at a higher rate than the pure substance. These substances are represented in numerous groups of medicaments such as in anti-hypertensives, anti-inflammatories, anti-anxiety agents, antidepressives, corticosteroids and antibactericides.

Particularly important examples of these substances are diazepam, digoxin, griseofulvin, methylhydroxyprogesterone acetate, nifedipine, megestrol acetate, haloperidol, nicardipine, diltiazem and etoposide.

The solvents usable for the active substances are water, organic solvents, oils and molten semisolids, of which those preferred are chloroform, acetone, dichloroethane and ethyl alcohol. The solvent choice is made on the basis of the characteristics required for the composition.

Any substance compatible with the medicament can be used as the microporous support, for example silicas, silicates, zeolites, aluminas, activated carbons and microporous polymer substances.

The microporous supports must have an average pore diameter of between 5 and 150 nm and preferably between 7 and 110 nm, with a specific surface of between 30 and 600 m²/g and a particle diameter of less than 200 µm.

The active substance concentration in the solution depends on the solvent used and is preferably close to the saturation concentration. For example using chloroform, the concentration is between 2 and 40 g/l and preferably between 30 and 35 g/l, and the quantity of microporous support added is between 3 and 500 grams per liter of solution and preferably between 50 and 250 grams per liter of solution. After stirring the suspension, the solvent is removed by slow evaporation at a temperature of 10°–20° C. less than the solution boiling point and at a pressure of between 500 and 760 mmHg (66.500–101.000 Pa).

The solid material obtained is disintegrated until a powder is obtained with a particle size of less than 200 microns and is heated in an oven at 20°–30° C. under vacuum to remove the solvent traces.

In the composition obtained in this manner the active substance has nanocrystal dimensions with a diameter of between 3 and 100 nm, and a melting point less than that of the same solid of coarser dimensions.

The pharmaceutical compositions according to the invention have the following advantages over compositions obtained by known methods:

(a) improved biopharmaceutical properties of the medicament due to its increased solubility which is related to the reduction in crystal dimensions by the known Kelvin equation:

$$\frac{S^*}{S} = \exp\left(\frac{2\gamma v}{RTr^*}\right)$$

where $S^*$ is the solubility of finely divided crystals of radius $r^*$, $S$ is the solubility of crystals of the same solid but of coarse dimensions, $\gamma$ is the solid/liquid interfacial tension, $v$ is the molar volume of the solid, $R$ is the universal gas constant and $T$ is the absolute temperature;

(b) in parallel with the lowering of the melting point of the medicament there are also considerable modifications in the rate of release of the medicament, which is more prolonged and controlled (release mechanism of zero order);

(c) compared with systems containing the medicament in amorphous form, the compositions according to the invention containing the crystalline medicament with a lowered melting point not only have improved dissolving characteristics but also have increased chemical and physical stability. In this respect it is well known that amorphous products tend to crystallize with time, with resultant deterioration in their passage into solution.

The compositions according to the present invention can be used for preparing capsules, pharmaceutical forms for topical use, suppositories, tablets and transdermal films, and can contain the conventional excipients such as binding agents, fillers, lubricants, disintegrating agents, wetting agents, flavorings and colorants. For example they can contain substances such as gelatin, sorbitol, lactose, starch, magnesium stearate and sodium lauryl sulphate.

The following examples of the preparation and characteristics of the compositions according to the invention are given by way of non-limiting illustration.

EXAMPLE 1

A solution of griseofulvin in chloroform and a solution of methylhydroxyprogesterone acetate (MHPA) in chloroform were prepared with a concentration of 35 g/l and 150 g/l respectively. 50 g of microporous silica gel with average pore radius 3.3 nm, specific surface 497.6 m$^2$/g and particle size between 8 and 200 microns were added to 1 liter of griseofulvin solution and to 200 ml of MHPA solution.

In each case, the suspension obtained was kept stirring at ambient temperature for 96 hours. The solvent was then removed by evaporation at a temperature of 45° C. and a pressure of 700 mmHg (93.100 Pa) in a rotary evaporator until a product of powder form was obtained. This product was disintegrated to a particle size of between 8 and 200 microns and heated in an oven to 30° C. under vacuum for 12 hours to eliminate all solvent traces.

The product obtained was subjected to the active substance release test using the USP XX paddle method under sink conditions, with 900 ml of buffer solution of pH 7.5 for the griseofulvin and of pH 5.5 for the MHPA, at 37° C. and at 150 r.p.m.

The product was also subjected to differential thermal analysis (D.S.C.) to determine its melting point and crystal size.

The thermal and dimensional characteristics of the two preparations are given in the following table:

|  | melting point (°C.) | -ΔT on original medicament (°C.) | Crystal diameter (nm) |
| --- | --- | --- | --- |
| Preparation with griseofulvin | 123 | 96.8 | 4.0 |
| Preparation with MHPA | 113.5 | 92.6 | 5.2 |

The results of the dissolving test are given in the following table:

| Time (minutes) | (a) griseofulvin in solution (μg/ml) | (b) MHPA in solution (μg/ml) |
| --- | --- | --- |
| 30 | 1.45 | 0.12 |
| 60 | 2.10 | 0.17 |
| 90 | 2.75 | 0.22 |
| 120 | 3.25 | 0.26 |

EXAMPLE 2

(Comparison)

Example 1 was repeated but with the difference that the suspension of microporous silica in the solution of active substance was kept stirring for 24 hours.

The thermal and dimensional characteristics of the two products are given in the following table:

|  | melting point (°C.) | -ΔT on original medicament (°C.) | Crystal diameter (nm) |
| --- | --- | --- | --- |
| Preparation with griseofulvin | 206.2 | 13.6 | 30.0 |
| Preparation with MHPA | 198.5 | 7.6 | 40.0 |

The results of the active substance release test are given in the follwoing table:

| Time (minutes) | (a) griseofulvin in solution (μg/ml) | (b) MHPA in solution (μg/ml) |
| --- | --- | --- |
| 30 | 1.60 | 0.13 |
| 60 | 2.50 | 0.20 |
| 90 | 3.61 | 0.29 |
| 120 | 4.55 | 0.37 |

EXAMPLE 3

Example 1 was repeated but with the difference that a microporous silica was used having an average pore radius of 7.7 nm.

The thermal and dimensional characteristics of the medicament crystals contained in the two products are given in the following table:

|  | melting point (°C.) | -ΔT on original medicament (°C.) | Crystal diameter (nm) |
| --- | --- | --- | --- |
| Preparation with griseofulvin | 184.8 | 35.0 | 10.8 |
| Preparation with MHPA | 169.9 | 36.2 | 15.1 |

The results of the active substance release test are given in the following table:

| Time (minutes) | (a) griseofulvin in solution (μg/ml) | (b) MHPA in solution (μg/ml) |
| --- | --- | --- |
| 30 | 1.45 | 0.12 |
| 60 | 2.10 | 0.17 |
| 90 | 2.75 | 0.22 |
| 120 | 3.25 | 0.26 |

EXAMPLE 4
(Comparison)

Example 3 was repeated but with the difference that the suspension of microporous silica in the solution of active substance was kept stirring for 24 hours.

The thermal and dimensional characteristics of the medicament crystals contained in the two products are given in the following table:

|  | melting point (°C.) | -ΔT on original medicament (°C.) | Crystal diameter (nm) |
| --- | --- | --- | --- |
| Preparation with griseofulvin | 206.2 | 13.6 | 30.0 |
| Preparation with MHPA | 198.5 | 7.6 | 40.0 |

The results of the active substance release test are given in the follwoing table:

| Time (minutes) | (a) griseofulvin in solution (μg/ml) | (b) MHPA in solution (μg/ml) |
| --- | --- | --- |
| 30 | 2.75 | 0.22 |
| 60 | 4.30 | 0.35 |
| 90 | 5.25 | 0.42 |
| 120 | 5.70 | 0.46 |

EXAMPLE 5

35 g of microporous silica gel with an average pore radius of 7.7 nm were added to 1 liter of a solution of griseofulvin in acetone at a concentration of 25 g/l. The suspension obtained was kept stirring at ambient temperature for 96 hours and the solvent was then removed by evaporation at 35° C. and a pressure of 600 mmHg (79.800 Pa) in a rotary evaporator until a product of powder form was obtained.

This product was disintegrated to a particle size of between 8 and 200 microns and left under vacuum at ambient temperature for 12 hours to eliminate solvent traces.

The product obtained is in the form of crystals with a melting point of 203.5° C. and a size of 25 nm. The results of the active substance release test are given in the following table:

| Time (minutes) | griseofulvin in solution (μg/ml) |
| --- | --- |
| 30 | 2.00 |
| 60 | 3.30 |
| 90 | 4.35 |
| 120 | 5.28 |

EXAMPLE 6

70 g of microporous silica gel with an average pore radius of 7.7 nm were added to 1 liter of a solution of griseofulvin in 1,2-dichloroethane at a concentration of 50 g/l. The suspension obtained was kept stirring at ambient temperature for 96 hours and the solvent was then removed by evaporation at 60° C. and a pressure of 500 mmHg (66.500 Pa) in a rotary evaporator until a product of powder form was obtained.

This product was disintegrated to a particle size of between 8 and 200 microns and left under vacuum at ambient temperature for 12 hours to eliminate solvent traces.

The product obtained is in the form of crystals with a melting point of 219.8° C. (same melting point as original medicament) and a size of the order of microns.

The results of the active substance release test are given in the following table:

| Time (minutes) | griseofulvin in solution (μg/ml) |
| --- | --- |
| 30 | 1.60 |
| 60 | 2.15 |
| 90 | 2.50 |
| 120 | 2.70 |

What is claimed is:

1. Pharmaceutical compositions comprising a microporous support having pores of an average diameter of between 5 and 150 nm, a surface area of between 30 and 600 m$^2$/g, and a particle diameter of less than 200 microns, said microporous support being selected from the group consisting of silica, silicates, zeolites, alumina, activated carbon and a microporous polymer, said microporous support having a pharmaceutically active substance selected from the group consisting of antihypertensive, antiinflammatory, antianxiety, antidepressive, corticosteroids and antibacterial medicaments distributed within the support pores in crystalline form, the crystal dimensions being in the nanometer range.

2. Compositions as claimed in claim 1, wherein said active substance crystal dimensions are between 3 and 100 nm.

3. Compositions as claimed in claim 1, wherein the content of said active substance is between 4 and 60% by weight.

4. Compositions as claimed in claim 1, wherein the active substance's crystal dimensions are between 3 and 100 nanometers and the content of the active substance is between 4 and 60% by weight.

5. Compositions as claimed in claim 1, wherein the active substance is selected from the group consisting of diazepam, digoxin, griseofulvin, methylhydroxy-progesterone acetate, nifedipine, megestrol acetate, haloperidol, nicardipine, diltiazem and etoposide.

6. Compositions as claimed in claim 1, comprising excipients selected from the group consisting of gelatin, sorbitol, lactose, starch, magnesium stearate and sodium lauryl sulphate.

7. A method for preparing pharmaceutical compositions, comprising adding a microporous support, having pores of an average diameter of between 5 and 150 nm, a surface area of between 30 and 600 m$^2$/g, and a particle diameter of less than 200 microns, and being selected from the group consisting of silica, silicates, zeolites, alumina, activated carbon and a microporous polymer, to a solution of a pharmaceutically active substance selected from the group consisting of antihypertensive, antiinflammatory, antianxiety, antidepressive, corticosteroids and antibacterial medicaments, stirring at ambient temperature for at least 70 hours, then slowly evaporating the solvent at a temperature of 10°-20° C. less than the solution boiling point in a pressure of between 500 and 760 mmHg.

8. A method as claimed in claim 7, wherein said active substance is a substance of low water solubility.

9. A method as claimed in claim 7, wherein the solvent for the solution of the active substance is selected from the group consisting of water, organic solvents, oils and molten semisolids, chloroform, acetone, dichloroethane, and ethyl alcohol.

10. A method as claimed in claim 7, wherein the active substance concentration in the solution is between 2 and 40 g/l.

11. A method as claimed in claim 7, wherein the quantity of the microporous support added to the solution is between 3 and 500 grams per liter of solution.

12. A method as claimed in claim 7, wherein said stirring at ambient temperature is conducted for 90-100 hours.

13. A method as claimed in claim 7, wherein the active substance is selected from the group consisting of diazepam, digoxin, griseofulvin, methylhydroxy-progesterone acetate, nifedipine, megestrol acetate, haloperidol, nicardipine, diltiazem and etoposide.

* * * * *